United States Patent [19]

Katz et al.

[11] 4,226,609

[45] Oct. 7, 1980

[54] SELECTED 3-TRICHLOROMETHYL-5-CYCLIC AMINE-1,2,4-THIADIAZOLE COMPOUNDS AND THEIR USE AS AMMONIUM NITRIFICATION INHIBITORS

[75] Inventors: Lawrence E. Katz, Orange; Walter A. Gay, Cheshire; Hansjuergen A. Schroeder, Hamden, all of Conn.

[73] Assignee: Olin Corporation, New Haven, Conn.

[21] Appl. No.: 16,589

[22] Filed: Mar. 1, 1979

[51] Int. Cl.$^3$ .................... C07D 417/04; C05C 11/00
[52] U.S. Cl. ........................... 71/64 F; 71/64 SC; 544/60; 544/134; 544/215; 544/335; 544/367; 546/209; 548/128; 260/245.5
[58] Field of Search ............... 544/134, 60, 215, 335, 544/367; 71/64 SC, 64 F; 546/209; 548/128; 260/245.5

[56] References Cited

U.S. PATENT DOCUMENTS

| | | | |
|---|---|---|---|
| 3,135,594 | 6/1964 | Goring | 71/11 |
| 3,542,537 | 11/1970 | Hanson | 71/1 |
| 3,904,619 | 9/1975 | D'Amico | 260/246 B |
| 4,078,912 | 3/1978 | Hawkins | 71/28 |

FOREIGN PATENT DOCUMENTS 47-4964 2/1972 Japan .

OTHER PUBLICATIONS

Sommer, "Landwirt, Forsch, Sonderh," 27(1926), 64–82.

*Primary Examiner*—Henry R. Jiles
*Assistant Examiner*—R. W. Ramsuer
*Attorney, Agent, or Firm*—William A. Simons; Thomas P. O'Day

[57] ABSTRACT

Disclosed are selected 3-trichloromethyl-5-cyclic amine-1,2,4-thiadiazole compounds. These compounds can be applied to or spread upon soil by themselves or in inert carriers or with nitrogen-containing fertilizers to inhibit ammonium nitrification in the soil.

36 Claims, No Drawings

SELECTED 3-TRICHLOROMETHYL-5-CYCLIC AMINE-1,2,4-THIADIAZOLE COMPOUNDS AND THEIR USE AS AMMONIUM NITRIFICATION INHIBITORS

BACKGROUND OF THE INVENTION

1. Field of the Invention

The present invention relates to selected 3-trichloromethyl-5-cyclic amine-1,2,4-thiadiazole compounds as compositions of matter. Furthermore, the present invention relates to nitrogenous fertilizer compositions containing one or more of these compounds. Still further, the present invention relates to the use of these compounds to inhibit the nitrification of ammonium nitrogen present in the soil.

2. Description of the Prior Art

The use of nitrogenous fertilizers (e.g., liquid ammonia, urea, ammonium salts such as ammonium sulfate, ammonium nitrate and ammonium phosphate, and the like) to improve plant nutrition and growth is well-known. These nitrogenous fertilizers, upon addition to the soil, from ammonium ions, which act as a suitable nitrogen source for cultivated crops. Specifically, because these ammonium ions are generally adsorbed and retained by clay and decomposing vegetation in the soil, they remain readily available for plant utilization.

However, through the bacterial process of nitrification, ammonium ions are converted to nitrates. Although nitrates are beneficial in some situations, they have, as anions not bound to soil colloids, the undesirable characteristic of being washed or leached away easily by rain or irrigation. Thus, situations where relatively rapid nitrification of the ammonium ions is accompanied by rain or irrigation may cause a great waste of fertilizer.

To be more specific, nitrification is the process whereby ammonium-nitrogen is converted to nitrite-nitrogen and then nitrate-nitrogen. This oxidation is carried out by various microorganisms called nitrifiers as illustrated by the following sequence:

The addition of chemical agents to the soil in order to inhibit or suppress the nitrification process and, thus, retain the nitrogen in the cationic ammonium form in the soil is well known. Such chemical agents are generally called nitrificides or nitrification inhibitors. These chemicals are toxic to the microorganism nitrifiers and will slow down or completely block the oxidation of ammonium ions to nitrates in the soil. More specifically, it is known that there are three types of nitrification inhibitors, namely, ammonium nitrification inhibitors; nitrite nitrification inhibitors; and ammonium-nitrite nitrification inhibitors. Ammonium nitrification inhibitors have been found to be the most commercially important of the three types because they have a positive effect, as compared to the other two types, on the nitrogen balance of soils and of many plants. See Sommer, K. *Nitrificides, Landwirt. Forsch. Sonderh. Volume* 27, pages 64–82 (1972) for a more detailed discussion of these three types of inhibitors.

In particular, it was pointed out in this article by Sommer that 3-trichloromethyl-5-ethoxy-1,2,4-thiadiazole is a very effective ammonium nitrification inhibitor. Besides having this beneficial activity, it was known that this compound is a soil fungicide. See U.S. Pat. No. 3,260,725, which issued to H. A. Schroeder on July 12, 1966. Consequently, the use of this particular compound in the soil has a valuable double action. This compound, however, has one shortcoming as a nitrification inhibitor, namely, that it is unstable in liquid ammonia solutions. Accordingly, it can not be applied as a nitrification inhibitor to the soil in the increasingly more popular liquid ammonia solutions.

Another recent development in the employment of other 1,2,4-thiadiazole compounds as nitrification inhibitors was disclosed in Japanese Patent Publication No. 4962/72, published Feb. 12, 1972, wherein it was taught that selected 3-trichloromethyl-5-non-cyclic amine-1,2,4-thiadiazoles may be used as nitrification inhibitors. However, as shown in the comparison examples cited in Table 4, below, the nitrification-inhibiting activity of these prior art compounds at the commercially-used amounts of 1.0 part per million parts by weight of soil is generally unsatisfactory.

Accordingly, it is believed that there still exists a need in this art for ammonium nitrification inhibitors which have a commercially suitable activity while being soluble and stable in liquid ammonia fertilizers. Furthermore, it would be highly desirable if such chemicals also had a relatively low vapor pressure so they would not vaporize readily into the atmosphere; not be easily washed away from soil by water; be non-toxic to man, livestock and plants; and, finally, be relatively inexpensive. It is believed that compounds within the scope of the present invention have all of these desirable characteristics.

BRIEF SUMMARY OF THE INVENTION

The present invention is directed to, as compositions of matter, selected 3-trichloromethyl-5-cyclic amine-1,2,4-thiadiazole compounds of the formula:

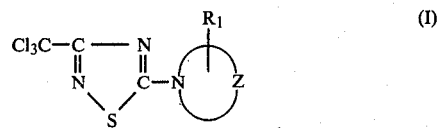

wherein

is either a 3, 4, 5, 6 or 7 membered saturated heterocyclic ring containing 1 to 3 hetero ring atoms; wherein Z comprises 2–6 carbon atoms and 0–2 hetero atoms, said hetero atoms being either nitrogen, oxygen or sulfur; and wherein the ring substituents $R_1$ are selected from the group consisting of hydrogen, hydroxy, nitro, cyano, halo, alkyl, haloalkyl, amino, alkylamino, dialkylamino and alkoxy groups.

Furthermore, the present invention is directed to, as compositions of matter, nitrogen-containing fertilizers incorporating these thiadiazole compounds of formula (I). Still further, the present invention is also directed to the use of these compounds as effective ammonium nitrification inhibitors.

DETAILED DESCRIPTION

Representative compounds of the present invention wherein the

saturated heterocyclic ring contains only nitrogen and carbon atoms including 3-trichloromethyl-5-(1-aziridinyl)-1,2,4-thiadiazole; 3-trichloromethyl-5-(1-azetidinyl)-1,2,4-thiadiazole; 3-trichloromethyl-5-(1-pyrrolidinyl)-1,2,4-thiadiazole; 3-trichloromethyl-5-(1-piperidino)-1,2,4-thiadiazole; 3-trichloromethyl-5-(1-homopiperidino)-1,2,4-thiadiazole; 3-trichloromethyl-5-(1-piperazinyl)-1,2,4-thiadiazole; 3-trichloromethyl-5-(1-imidazolidinyl)-1,2,4-thiadiazole; 3-trichloromethyl-5-(1-hexahydro-s-triazinyl)-1,2,4-thiadiazole; 3-trichloromethyl-5-(1-homopiperazinyl)-1,2,4-thiadiazole; 3-trichloromethyl-5-(1-hexahydropyrimidinyl)-1,2,4-thiadiazole; and their derivatives thereof wherein the heterocyclic ring substituents $R_1$ are not all hydrogens. A preferred class of these nitrogen and carbon atom-containing heterocyclic ring compounds may be illustrated by the following formula (II):

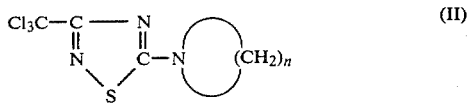

wherein n is 2, 3, 4, 5 or 6. The first five chemical names recited immediately above are the respective names for this preferred class of compounds.

Representative compounds of the present invention wherein the

saturated heterocyclic ring contains nitrogen, carbon and oxygen atoms including 3-trichloromethyl-5-(1-morpholinyl)-1,2,4-thiadiazole and 3-trichloromethyl-5-[1-(hexahydro-1,4-oxazepinyl)]-1,2,4-thiadiazole and their derivatives wherein the heterocyclic ring substituents $R_1$ include groups other than hydrogen. The 5-morpholinyl compound is one of the most preferred compounds of the present invention because of its low cost and excellent activity as an ammonium nitrification inhibitor. Besides those desirable characteristics, this compound also has a relatively low vapor pressure. Furthermore, this 5-morpholinyl compound is not appreciably water soluble and, thus, will not be readily washed away or leached by rain water or irrigation water. Advantageously, this compound has been found to be soluble and stable in ammonia, thus making it suitable in liquid ammonia fertilizers. Still further, this compound is soluble in many organic solvents, such as xylene, which are widely used for many agricultural formulations. Also, this 5-morpholinyl compound has not shown any phytotoxic properties, but does have some nematocidal activity. The toxicological properties of this compound have not been determined at the present time. But, by analogy to the known safe toxicological properties of 3-trichloromethyl-5-ethoxy-1,2,4-thiadiazole, it is believed that this compound should be relatively non-toxic to man, livestock and cultivated crops.

Representative compounds of the present invention wherein the

heterocyclic ring contains nitrogen, carbon and sulfur compounds including 3-trichloromethyl-5-(1-thiomorpholinyl)-1,2,4-thiadiazole and its derivatives wherein the heterocyclic ring substituents $R_1$ include groups other than hydrogen.

The preferred heterocyclic ring substituents $R_1$ for the present invention include hydrogen, hydroxy, nitro, cyano, chloro, fluoro, lower alkyl groups from 1 to 4 carbon atoms (e.g., methyl, ethyl and n-butyl), trichloromethyl, trifluoromethyl, amino, lower alkylamino groups having 1 to 4 carbon atoms (e.g., methylamine and ethylamine), di-(lower alkyl) amine groups having 1 to 4 carbon atoms (e.g., dimethylamine, diethylamine), and lower alkoxy groups having from 1 to 4 carbon atoms (e.g., methoxy and ethoxy).

It should be noted that the present invention is directed to having a saturated (i.e., where the carbon-carbon bonds in the ring are single bonds) heterocyclic amine in the 5-position of the present compound; as opposed to having an unsaturated ring (e.g., where one or more of the carbon-carbon bonds in the ring may be double or triple) or an aromatic ring. However, applicants do not suggest that these latter classes of compounds may not also have nitrification-inhibiting activity.

The compounds of the present invention may be prepared by reacting 3-trichloromethyl-5-chloro-1,2,4-thiadiazole with the desired cyclic secondary amine as illustrated in the following Equation (A) wherein morpholine is the selected cyclic amine.

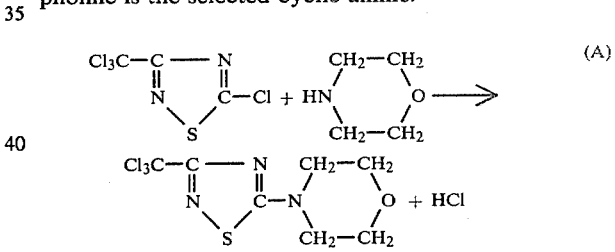

3-Trichloromethyl-5-chloro-1,2,4-thiadiazole is described in U.S. Pat. No. 3,260,725, which issued to H. A. Schroeder on July 12, 1966, and is made by reacting trichloroacetamidine with trichloromethane sulfenyl chloride in the presence of a base such as sodium hydroxide.

The heterocyclic secondary amine reactants are generally commercially available or are made by various known synthesis methods. For example, morpholine may be made by dehydration of diethanolamine. Also, piperidine may be made by cyclization of 1,5-diaminopentane.HCl or reduction of pyridine.

Any conventional reaction conditions known for reacting a halide compound like 3-trichloromethyl-5-chloro-1,2,4-thiadiazole with secondary amine compounds may be used. Preferably, it is desirable to use a molar excess of the amine or, alternatively, carry the reaction out in the presence of inorganic base such as sodium carbonate, in order to neutralize the hydrogen halide generated by this reaction.

In the case of employing a molar excess of the amine, it is preferable to use from about 1.25 to about 5 moles, more preferably, from about 2 to about 3 moles, of the secondary amine for each mole of 3-trichloromethyl-5-chloro-1,2,4-thiadiazole compound. In the situation where inorganic base is also employed, it is preferable to employ about 1 to about 2 moles of the secondary amine and about 1 to about 3 moles of an inorganic base such as sodium carbonate. Suitable reaction temperatures may range from about 5° C. to about 140° C., depending upon the secondary amine, the type of solvent, if any, employed and other reaction conditions. Suitable reaction times may range from about 5 minutes to about 500 minutes, depending upon temperature, solvent, if any, and other reaction conditions.

This reaction may be carried out in the presence of any suitable inert solvent. However, it is not limited to the use of a solvent or any particular solvent. It is believed that suitable inert solvent would include ether, tetrahydrofuran, methylene chloride, chloroform, carbon tetrachloride, benzene, xylene, toluene, acetone, ethanol, and ethyl acetate. As shown in the laboratory examples below, ether is conveniently employed. On a large commercial scale, other solvents may be more preferable.

Any suitable product recovery means may be employed to recover the products of the present invention from the reaction mixture illustrated by Equation (A), above. If a molar excess of the amine and an inert solvent are used, for example, then it may be desirable to first cool the reaction mixture to precipitate the amine hydrochloride salt which may be formed as a by-product. Next, this precipitate is removed by filtration or other suitable means. The remaining clear solution of solvent and product is subjected to any convenient means to remove the solvent such as stripping under reduced pressure. The crude product thus formed may be recrystallized by employing a suitable solvent such as ligroin. After this recrystallization, the pure product formed may be used immediately for the uses described below or may be stored for future uses.

In accordance with the present invention, it has been found that the 3-trichloromethyl-5-cyclic amine-1,2,4-thiadiazole compounds of formula (I), above, either singly or in mixtures thereof, can be utilized as nitrification inhibitors.

In practicing the process of the present invention, soil may be treated with an effective nitrification-inhibiting amount of these above-mentioned compounds. It is to be understood that the term "effective nitrification-inhibiting amount" as used in the specification and claims herein is intended to include any amount that will inhibit or suppress the nitrification of ammonium-nitrogen in the soil and therefore promote desirable plant growth and nutrition therein. Of course, this amount may be constantly changing because of the possible variations of many parameters. Some of these may include the pH of the soil, soil temperature, trace metals and other constituents in the soil, degree of effectiveness required, weather conditions, time of application, amount of fertilizer applied, crops involved and type of carrier, if any. For most uses, an effective nitrification-inhibiting amount would range from about 0.1 to 500 parts per million relative to the soil being treated. Of course, the amount applied should be insufficient to provide toxicity to plants. Usually, a good practice is to add from about 0.1 to about 10 pounds of these compounds to an acre of crop land.

This step of treating soil may be accomplished by applying these compounds into the soil or on its surface by themselves in any conventional manner, combining these compounds with an inert carrier or other substance which may enhance the effectiveness of the chemical or facilitate handling. Moreover, the pesticidal and biocidal activity of the present compounds may be broadened by the addition thereto of other known fungicides, herbicides, insecticides, nematocides, biocides and the like.

If the above-mentioned compounds of the present invention are combined with a solid or liquid inert carrier before application, then any known methods for formulating and applying these active compounds may be employed. Included in such known methods are applications in the form of dusts, dust or emulsion concentrates, wettable powders and concentrates, granulates, dispersions, sprays, solutions and the like.

The dusts are usually prepared by simply grinding together from about 1% to 15% by weight of any of these active compounds with a finely divided inert diluent such as walnut flour, diatomaceous earth, fullers earth, attaclay, talc or kaolin. Dust concentrates are made in similar fashion excepting that about 16% to 75% by weight of active compound is ground usually together with the diluent. In practice, dust concentrates are then generally admixed at the site of use with more inert diluent before it is applied to the soil.

Wettable powders are generally prepared in the same manner as dust concentrates, but usually about 1% to 10% by weight of a dispersing agent, for example, an alkali metal lignosulfonate and about 1% to 10% of a surfactant, such as a non-ionic surfactant, are incorporated in the formulation.

Emulsifiable liquids may be prepared by dissolving the active compound in an organic solvent, such as xylene or acetone, and admixing the thus formed solution with a surfactant or an emulsifier. The emulsified liquid is then generally dispersed in water for spray application to the soil.

Granulates are formulated generally by a method where these active compounds are dissolved in an organic solvent and the resulting solution is then applied to a granulated mineral or the like (e.g., bentonite, $SiO_2$, or the like) followed by evaporating off the organic solvent. Granulates can also be obtained by the compacting of the carrier material with the active substance and then reducing this compacted material in size.

Furthermore, the applied formulations of the present invention include other liquid preparations such as dispersions, sprays or solutions. For these purposes, one or more of the above-mentioned active compounds is normally dissolved in a suitable organic solvent, solvent mixtures or water. As organic solvents, it is possible to use any suitable aliphatic and aromatic hydrocarbon or their derivatives. It is preferred that the solvent be odorless and, moreover, be inert to the active compound.

It should be clearly understood that any of the above-named formulations, the ingredients which may make up such formulations other than the active compounds and their dosages, and means of applying these formulations may include all known and conventional substances, amounts and means, respectively, that are suitable for obtaining the desired nitrification-inhibiting result. Therefore, such process parameters are not critical to the present invention.

Besides the inert solid or liquid carriers mentioned above, the active compounds of the present invention may be employed in combination with a nitrogen-containing fertilizer. Specifically, the present invention encompasses the use of effective nitrification-inhibiting amount of one or more of these active compounds either before or after or simultaneously with one or more nitrogen-containing fertilizers. The term "nitrogen-containing fertilizer" includes any and all known fertilizers that contain nitrogen including ammonia, aqueous ammonia, ammonium hydroxide in solution, ammonium salts such as the sulfate, nitrate and phosphate salts, urea, NPK fertilizers containing one or more ammonium salts and/or urea, and any other materials known to be sources of ammonium ions in soil.

If the present active compounds are combined and applied to the soil with a nitrogen-containing fertilizer, any conventional method of formulation and fertilizer application may be employed. For example, the active compound may be added to a simple or compound solid fertilizer and ground together to form a homogeneous mixture. Alternatively, the active compound may be sprayed onto the surface of the particulate fertilizer to form a coating. Such mixtures of solid fertilizers and active compound may be in the form of solid powders, crystals, pills, granules and the like. If the active compound is added to a liquid fertilizer like liquid ammonia then simply dissolving the compound in the fertilizer should suffice. The effective nitrification-inhibiting amount of the active compound will, of course, vary with each fertilizer composition and application. Generally, the employment of from about 0.1% to about 25% by weight of the nitrogen content of fertilizer applied to the soil.

The following examples further illustrate the present invention. All parts and percentages employed therein are by weight unless otherwise indicated.

EXAMPLE 1

3-Trichloromethyl-5-(1-Piperidino) 1,2,4-Thiadiazole

To 17.1 grams (0.2 mole) piperidine in 100 milliliters ether was added 23.8 grams (0.1 mole) 3-trichloromethyl-5-chloro-1,2,4-thiadiazole in 100 milliliters ether. The solution was refluxed with stirring for one hour after addition. Filtration to remove salt by-products yielded a clear filtrate which was concentrated on a steam bath to give 28.9 grams (99% molar yield) of oil which solidified on cooling to room temperature. Recrystallization from ligroin yielded white solid (melting point 78°–78.5° C.). The structure was confirmed via infrared and elemental analysis.

Analysis for $C_8H_{10}N_3Cl_3S$:

|  | C | H | N | Cl | S |
|---|---|---|---|---|---|
| Calculated | 33.52 | 3.52 | 14.66 | 37.11 | 11.19 |
| Found | 33.47 | 3.42 | 14.89 | 37.32 | 11.01 |

EXAMPLE 2

3-Trichloromethyl-5-(1-Pyrrolidinyl)-1,2,4-Thiadiazole

To 14.2 grams (0.2 mole) pyrrolidine in 100 milliliters ether was added 23.8 grams (0.1 mole) 3-trichloromethyl-5-chloro-1,2,4-thiadiazole in 100 milliliters ether. The solution was refluxed with stirring for one hour after addition. Filtration to remove salt by-products yielded a clear filtrate which was concentrated on a steam bath to give 16.4 grams (60% molar yield) of white solid. Recrystallization from ligroin yielded a pure product (melting point 105.5°–107° C.). The structure was confirmed via infrared and elemental analysis. Analysis for $C_7H_8N_3Cl_3S$:

|  | C | H | N | Cl | S |
|---|---|---|---|---|---|
| Calculated | 30.84 | 2.96 | 15.42 | 39.02 | 11.76 |
| Found | 30.78 | 2.86 | 15.63 | 39.24 | 11.65 |

EXAMPLE 3

3-Trichloromethyl-5-(1-Morpholinyl)-1,2,4-Thiadiazole

To 17.4 grams (0.2 mole) morpholine in 100 milliliters ether was added 23.8 grams (0.1 mole) 3-trichloromethyl-5-chloro-1,2,4-thiadiazole in 100 milliliters ether. The solution was refluxed with stirring for one hour after addition. Filtration to remove salt by-products yielded a clear filtrate which was concentrated to give 24.6 grams of white solid. The solid by-product, removed in the initial filtration, was washed with water and dried to give 3.8 grams more product. The combined product was 28.4 grams (98% molar yield). Recrystallization from ligroin yielded pure solid (melting point 108° C.). The structure was confirmed via infrared and elemental analysis.

Analysis for $C_7H_8N_3Cl_3SO$:

|  | C | H | N | Cl | S |
|---|---|---|---|---|---|
| Calculated | 29.13 | 2.79 | 14.56 | 36.86 | 11.11 |
| Found | 29.04 | 2.79 | 14.76 | 36.97 | 10.98 |

EXAMPLE 4

3-Trichloromethyl-5-(1-Homopiperidino) 1,2,4-Thiadiazole

To 9.9 grams (0.1 mole) hexamethyleneimine in 50 milliliters ether was added 11.9 grams (0.05 mole) 3-trichloromethyl-5-chloro-1,2,4-thiadiazole in 50 milliliters ether. The solution was refluxed with stirring for one hour after addition. Filtration to remove salt by-products yielded a clear filtrate which was rotary evaporated under aspiration to yield 15.1 grams (99% molar yield) of white solid. Recrystallization from ligroin yielded pure product (melting point 70°–71° C.). The structure was confirmed via infrared and elemental analysis.

Analysis for $C_9H_{12}N_3Cl_3S$:

|  | C | H | N | Cl | S |
|---|---|---|---|---|---|
| Calculated | 35.95 | 4.02 | 13.98 | 35.38 | 10.67 |
| Found | 35.83 | 4.20 | 13.96 | 35.10 | 10.36 |

Soil Screen Evaluation with Fine Sand Soil from Texas

Three stock solutions containing 0.02 grams of each compound prepared by Examples 1, 2 and 3 in 10 milliliters of ethanol were made. 0.1 Milliliter of each stock solution was added (by microliter syringe) to 20 grams of Fine Sand Soil from Texas (see Table 3 for analysis) and mixed. To each of these three soil mixtures was added 3.9 milliliters of an aqueous ammonium sulfate solution which contained 3.984 grams of ammonium sulfate per liter of solution. The soil mixtures contained 1 part per million by weight of active compound, 200 parts per million ammonia concentration, and were saturated with water to 60% by weight of their field holding capacity (i.e., soil capacity to hold water). These mixtures were stirred for five minutes after the above additions and then incubated at 28° C. The caps on the jars holding these soil samples were opened daily to aerate the samples. After the desired incubation period (i.e., either 14 or 28 days), the soil samples were shaken with 200 milliliters water. The resulting soil and water mixtures were decanted, leaving a sediment behind, and then centrifuged to remove any remaining solids. Two milliliters of each clear solution were pipetted into a 10 milliliter volumetric flask. To these were added 0.3 milliliter of Nessler's Reagent[1] and sufficient water to obtain 10 milliliters of solution. The solutions were transferred to a U. V. cell and the percent transmittance read at 420 millimicrons (the peak of the desired complex being observed).

[1] The preparation is taught by J. H. Yoe, "Photometric Chemical Analysis" Volume 1 (Colorimetric Analysis), John Wiley and Sons, New York, N.Y., 1928, pp 306–309. This reagent is a well-known ammonia identification agent.

The percent transmittance values obtained were read off a standard percent transmittance curve made employing known ammonium sulfate solutions (blank aqueous soil extract was used as solvent) to determine ammonia concentration. The ammonia concentrations determined were then used to calculate the percent nitrification inhibition using the following formula:

$$\% \text{ Inhibition} = \frac{\text{Change in Control} - \text{Change in Sample}}{\text{Change in Control}} \times 100$$

Change in control was the difference between the initial ammonia concentration of 200 parts per million and the value determined after either 14 or 28 days of incubation using a blank sample (i.e., without the active compounds of Examples 1, 2 and 3).

Change in sample was the difference between the initial concentration of 200 parts per million and the ammonia value determined after either 14 or 28 days of incubation using samples containing said active compounds.

TABLE 1

| | Fine Sand Soil Screen | |
|---|---|---|
| | Nitrification Inhibition[2] | |
| Compound (at 1 ppm) | 14 Day Incubation | 28 Day Incubation |
| 5-(1-Piperidino) | 99% | 98% |
| 5-(1-Pyrrolidinyl) | 99% | 99% |
| 5-(1-Morpholinyl) | 99% | 88% |

[2] The values in this Table reflect an average of results of four duplicate runs.

Soil Screen Evaluation with Silt Loam Soil from Illinois

The screening procedure set forth above with the Texas soil was repeated utilizing silt loam soil from Illinois. (See Table 3 for soil characteristics.) To attain a 60% field holding capacity with this soil, 4.8 milliliters of an aqueous sulfate solution which contained 3.232 grams per liter of solution was employed instead. The percent nitrification inhibition is given in Table 2.

TABLE 2

| | Silt Loam Soil Screen | |
|---|---|---|
| | Nitrification Inhibition[3] | |
| Compound (at 1 ppm) | 14 Day Incubation | 28 Day Incubation |
| 5-(1-Piperidino) | 98% | 83% |
| 5-(1-Pyrrolidinyl) | 99% | 88% |

TABLE 2-continued

| | Silt Loam Soil Screen | |
|---|---|---|
| | Nitrification Inhibition[3] | |
| Compound (at 1 ppm) | 14 Day Incubation | 28 Day Incubation |
| 5-(1-Morpholinyl) | 94% | 88% |

[3] The values given in this Table represent an average of results obtained from four duplicate runs.

TABLE 3

| | Comparison of Soils | |
|---|---|---|
| Location | Texas | Illinois |
| pH | 7.2 | 5.2 |
| $NO_3$—N(ppm) | 25.0 | 12.0 |
| $NH_3$—N(ppm) | 12.0 | 12.0 |
| P (ppm) | 100.0 | 25.0 |
| K (ppm) | 250.0 | 150.0 |
| Ca (ppm) | 1050 | 1050 |
| Mg (ppm) | 90 | 18 |
| Al (ppm) | 10 | 10 |
| Mn (ppm) | 5 | 5 |
| Total Soluble Salts (ppm) | 850 | 500 |
| Sand (%) | 89.4 | 14.0 |
| Silt (%) | 7.0 | 72.0 |
| Clay (%) | 3.6 | 14.0 |
| Organic Matter (%) | 1.7 | 3.4 |
| Classification | Fine Sand | Silt Loam |
| Field Holding Capacity (milliliters/20 grams) | 6.5 | 6.8 |
| Total Heterotroph Population organisms/gram | $4.3 \times 10^6$ | $2.3 \times 10^6$ |
| Total Ammonia-Oxidizer Population organisms/gram | $1.2 \times 10^4$ | $2.3 \times 10^3$ |

Soil Screening Evaluation Comparisons

The screening procedure set forth above with Texas Soil was repeated with numerous 3-trichloromethyl-5-amine-1,2,4-thiadiazole compounds, which are not among the active compounds of the present invention. Table 4, below, shows the percent nitrification inhibition of each of these other compounds after 28 day of inhibition. It can be noted that the cyclic amine compounds of the present invention are generally more active than the compounds listed below.

TABLE 4

| 5-Amine Substituent | % Nitrification Inhibition[4] |
|---|---|
| —N(H)CH$_3$ | 0% |
| —N(H)—C$_6$H$_4$—CF$_3$ | 0% |
| —N(H)—C$_6$H$_3$Cl$_2$ | 0% |
| —N(H)—C$_6$H$_4$—CH$_3$ | 2% |
| —N(H)—C$_6$H$_4$—CH$_3$ | 17% |
| —NH$_2$ | 17% |

TABLE 4-continued

| 5-Amine Substituent | % Nitrification Inhibition[4] |
|---|---|
| —N(H)—⟨phenyl with 2 F⟩ | 31% |
| —N(CH$_2$CH$_3$)$_2$ | 74% |
| —N(H)—CH$_2$CH$_2$CH$_3$ | 93% |

[4] The values given in this Table represent an average of results obtained from two duplicate runs.

What is claimed is:

1. A 3-trichloromethyl-5-cyclic amine-1,2,4-thiadiazole compound of the formula:

$$Cl_3C-C=N, \quad N=C-N(R_1)Z \quad (\text{with } S \text{ bridge})$$

wherein $$-N\underset{Z}{\frown}$$

is either a 3, 4, 5, 6 or 7 membered saturated heterocyclic ring containing 1 to 3 hetero ring atoms; wherein Z comprises 2–6 carbon atoms and 0–2 hetero atoms, said hetero atoms being either nitrogen, oxygen or sulfur; and wherein the ring substituents R$_1$ are selected from the group consisting of hydrogen, hydroxy, nitro, cyano, halo, alkyl, haloalkyl, amino, alkylamino, dialkylamine and alkoxy groups.

2. The compound of claim 1 wherein said heterocyclic ring atoms are selected from the group consisting essentially of nitrogen and carbon.

3. The compound of claim 2 having the formula:

$$Cl_3C-C=N, \quad N=C-N(CH_2)_n \text{ (ring)}$$

wherein n is 2, 3, 4, 5 or 6.

4. The compound of claim 3 having the formula:

$$Cl_3C-C=N, \quad N=C-N\langle CH_2CH_2 / CH_2CH_2 \rangle$$

5. The compound of claim 3 having the formula:

$$Cl_3C-C=N, \quad N=C-N\langle CH_2-CH_2, CH_2, CH_2-CH_2 \rangle$$

6. The compound of claim 3 having the formula:

$$Cl_3C-C=N, \quad N=C-N\langle CH_2-CH_2-CH_2, CH_2-CH_2-CH_2 \rangle$$

7. The compound of claim 1 wherein said heterocyclic ring atoms are selected from the group consisting essentially of nitrogen, carbon and oxygen.

8. The compound of claim 7 having the formula:

$$Cl_3C-C=N, \quad N=C-N\langle CH_2-CH_2, O, CH_2-CH_2 \rangle$$

9. The compound of claim 1 wherein said heterocyclic ring atoms are selected from the group consisting of nitrogen, carbon and sulfur.

10. The compound of claim 9 having the formula:

$$Cl_3C-C=N, \quad N=C-N\langle CH_2-CH_2, S, CH_2-CH_2 \rangle$$

11. The compound of claim 1 wherein said ring substituents R$_1$ are selected from the group consisting of hydrogen, hydroxy, nitro, cyano, chloro, fluoro, lower alkyl groups having from 1 to 4 carbon atoms, trichloromethyl, trifluoromethyl, amino, lower alkyl amino groups having from 1 to 4 carbon atoms, di-(lower alkyl)amino groups with each lower alkyl group having from 1 to 4 carbon atoms, and lower alkoxy groups having from 1 to 4 carbon atoms.

12. The compound of claim 11 wherein all of said ring substituents R$_1$ are hydrogen.

13. A fertilizer composition comprising one or more nitrogen-containing fertilizers in admixture with an effective nitrification-inhibiting amount of one or more nitrification-inhibiting compounds of claim 1.

14. A fertilizer composition comprising one or more nitrogen-containing fertilizers in admixture with an effective nitrification-inhibiting amount of one or more compounds of claim 2.

15. A fertilizer composition comprising one or more nitrogen-containing fertilizers in admixture with an effective nitrification-inhibiting amount of one or more compounds of claim 7.

16. The fertilizer composition of claim 15 wherein said nitrification-inhibiting compound has the formula:

$$Cl_3C-C=N, \quad N=C-N\langle CH_2-CH_2, CH_2, CH_2-CH_2 \rangle$$

17. The fertilizer composition of claim 16 wherein said fertilizer is liquid ammonia.

18. A fertilizer composition comprising one or more nitrogen-containing fertilizers in admixture with an effective nitrification-inhibiting amount of one or more nitrification-inhibiting compounds of claim 9.

19. The fertilizer composition of claim 13 wherein said fertilizer is liquid ammonia.

20. A method for inhibiting the nitrification of ammonium-nitrogen in soil which comprises treating the soil with an effective nitrification-inhibiting amount of one or more nitrification-inhibiting compounds having the formula:

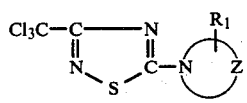

wherein

is either a 3, 4, 5, 6 or 7 membered saturated heterocyclic ring containing 1 to 3 hetero ring atoms; wherein Z comprises 2-6 carbon atoms and 0-2 hetero atoms, said hetero atoms being either nitrogen, oxygen, or sulfur; and wherein the ring substituents $R_1$ are selected from the group consisting of hydrogen, hydroxy, nitro, cyano, halo, alkyl, haloalkyl, amino, alkylamino, dialkylamino and alkoxy groups.

21. The method of claim 20 wherein said nitrification-inhibiting compound has a

heterocyclic ring with said ring atoms being selected from the group consisting essentially of nitrogen and carbon.

22. The method of claim 21 wherein said nitrification-inhibiting compound has the formula:

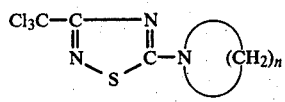

wherein n is 2, 3, 4, 5 or 6.

23. The method of claim 22 wherein said nitrification-inhibiting compound has the formula:

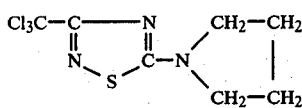

24. The method of claim 22 wherein said nitrification-inhibiting compound has the formula:

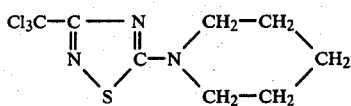

25. The method of claim 22 wherein said nitrification-inhibiting compound has the formula:

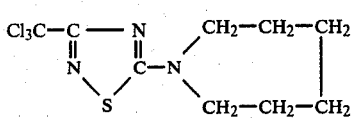

26. The method of claim 20 wherein said nitrification-inhibiting compound has a

heterocyclic ring with said ring atoms being selected from the group consisting essentially of nitrogen, carbon and oxygen.

27. The method of claim 26 wherein said nitrification-inhibiting compound has the formula:

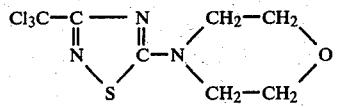

28. The method of claim 20 wherein said nitrification-inhibiting compound has a

heterocyclic ring with said ring atoms being selected from the group consisting essentially of nitrogen, carbon and sulfur.

29. The method of claim 28 wherein said nitrification-inhibiting compound has the formula:

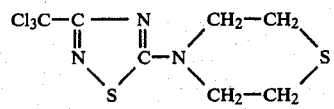

30. The method of claim 20 wherein said ring substituents $R_1$ are selected from the group consisting of hydrogen, hydroxy, nitro, cyano, chloro, fluoro, lower alkyl groups having from 1 to 4 carbon atoms, trichloromethyl, trifluoromethyl, amino, (lower alkyl) amino groups having from 1 to 4 carbon atoms, di-(lower alkyl) amino groups with each lower alkyl group having from 1 to 4 carbon atoms, and lower alkoxy groups having from 1 to 4 carbon atoms.

31. The method of claim 30 wherein all of said ring substituents $R_1$ are hydrogen.

32. The method of claim 20 wherein said treatment of soil by a nitrification-inhibiting compound is in conjunction with the addition of nitrogen-containing fertilizer to said soil.

33. The method of claim 32 wherein said nitrification-inhibiting compound and said fertilizer are added simultaneously to said soil.

34. The method of claim 33 wherein said fertilizer is in liquid form.

35. The method of claim 34 wherein said nitrification-inhibiting compound has a formula:

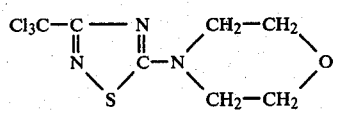

36. The method of claim 35 wherein said fertilizer is liquid ammonia.

* * * * *

UNITED STATES PATENT AND TRADEMARK OFFICE
CERTIFICATE OF CORRECTION

PATENT NO. : 4,226,609

DATED : October 7, 1980

INVENTOR(S) : Lawrence E. Katz, Walter A. Gay, and Hansjuergen A. Schroeder

It is certified that error appears in the above-identified patent and that said Letters Patent are hereby corrected as shown below:

In Column 1, line 23, delete "from" and insert --form--.

In Column 12, delete the formula of Claim 16 which reads:

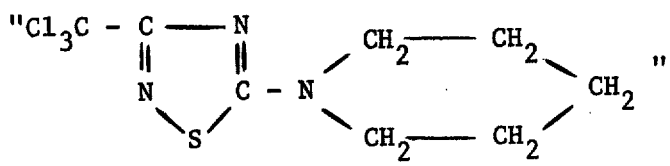

and insert

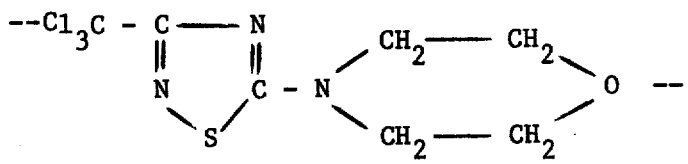

Signed and Sealed this

Twenty-third Day of December 1980

[SEAL]

Attest:

SIDNEY A. DIAMOND

Attesting Officer

Commissioner of Patents and Trademark